US010874332B2

(12) United States Patent
Glazer et al.

(10) Patent No.: US 10,874,332 B2
(45) Date of Patent: Dec. 29, 2020

(54) RESPIRATION MONITOR

(71) Applicant: UdiSense Inc., New York, NY (US)

(72) Inventors: Assaf Glazer, Hoboken, NJ (US);
Hadas Kaminsky-Glazer, Hoboken, NJ (US); Shaked Dovrat, Tel Aviv (IL);
Amnon Kami, New York, NY (US);
Tor Ivry, Rishon Lezion (IL); Amir Katz, Bat Hefer (IL); Mark Prommel, Montclair, NJ (US); Oscar Frias, New York, NY (US); Marco Perry, New York, NY (US); Natalie Louise Barnett, New York, NY (US); Yanai Victor Ankri, Netanya (IL); Yena Seo Lukac, New York, NY (US)

(73) Assignee: UDISENSE INC., New York, NY (US)

( * ) Notice: Subject to any disclaimer, the term of this patent is extended or adjusted under 35 U.S.C. 154(b) by 21 days.

(21) Appl. No.: 16/197,479

(22) Filed: Nov. 21, 2018

(65) Prior Publication Data

US 2019/0150798 A1    May 23, 2019

Related U.S. Application Data (60) Provisional application No. 62/589,587, filed on Nov. 22, 2017.

(51) Int. Cl.
*A61B 5/113* (2006.01)
*H04N 7/18* (2006.01)
(Continued)

(52) U.S. Cl.
CPC .......... *A61B 5/1135* (2013.01); *A61B 5/0064* (2013.01); *A61B 5/0816* (2013.01);
(Continued)

(58) Field of Classification Search
CPC ... A61B 5/1135; A61B 5/0064; A61B 5/0816; A61B 5/1128; A61B 5/6804;
(Continued)

(56) References Cited

U.S. PATENT DOCUMENTS

| D220,534 S | 4/1971 | Selden et al. |
| 3,938,500 A * | 2/1976 | Simmons ............... A61B 5/1118 |
| | | 600/559 |

(Continued)

FOREIGN PATENT DOCUMENTS

| CN | 204862242 U | 12/2015 |
| EP | 2292124 A1 | 3/2011 |

(Continued)

OTHER PUBLICATIONS

Dalal et al.,"Histograms of Oriented Gradients for Human Detection", IEEE Computer Society Conference on Computer Vision and Pattern Recognition (CVPR'05), 8 pages, 2005.

(Continued)

*Primary Examiner* — Nathan J Flynn
*Assistant Examiner* — Caroline Somera
(74) *Attorney, Agent, or Firm* — Kligler & Associates Patent Attorneys Ltd (57) ABSTRACT

A system for respiration monitoring includes a garment, which is configured to be fitted snugly around a body of a human subject, and which includes, on at least a portion of the garment that fits around a thorax of the subject, a pattern of light and dark pigments having a high contrast at a near infrared wavelength. A camera head is configured to be mounted in proximity to a bed in which the subject is to be placed, and includes an image sensor and an infrared illumination source, which is configured to illuminate the bed with radiation at the near infrared wavelength, and is configured to transmit a video stream of images of the subject (Continued)

US 10,874,332 B2

Page 2 in the bed captured by the image sensor to a processor, which analyzes movement of the pattern in the images in order to detect a respiratory motion of the thorax.

17 Claims, 5 Drawing Sheets (51) Int. Cl.
| | |
|---|---|
| H04N 5/33 | (2006.01) |
| G06T 7/246 | (2017.01) |
| G08B 21/04 | (2006.01) |
| A61B 5/00 | (2006.01) |
| A61B 5/08 | (2006.01) |
| A61B 5/11 | (2006.01) |
| A41B 13/06 | (2006.01) |

(52) U.S. Cl.
CPC .......... *A61B 5/1128* (2013.01); *A61B 5/6804* (2013.01); *A61B 5/6823* (2013.01); *A61B 5/6891* (2013.01); *A61B 5/746* (2013.01); *G06T 7/246* (2017.01); *G08B 21/0453* (2013.01); *H04N 5/33* (2013.01); *H04N 7/183* (2013.01); *H04N 7/188* (2013.01); *A41B 13/06* (2013.01); *A61B 5/0022* (2013.01); *A61B 5/7485* (2013.01); *G06T 2207/10048* (2013.01); *G06T 2207/30196* (2013.01)

(58) Field of Classification Search
CPC ..... A61B 5/6823; A61B 5/6891; A61B 5/746; A61B 5/0022; A61B 5/7485; G06T 7/246; G06T 2207/10048; G06T 2207/30196; G08B 21/0453; H04N 5/33; H04N 7/183; H04N 7/188; A41B 13/06
See application file for complete search history.

(56) References Cited

U.S. PATENT DOCUMENTS

| | | | |
|---|---|---|---|
| 4,047,684 A | 9/1977 | Kobayashi | |
| 4,240,603 A | 12/1980 | Chiariello | |
| D268,458 S | 4/1983 | Schoenig et al. | |
| 4,561,339 A | 12/1985 | Jensen | |
| D289,835 S | 5/1987 | Schoenig et al. | |
| 4,712,756 A | 12/1987 | Kester et al. | |
| D302,652 S | 8/1989 | Spaeth, Jr. | |
| D314,873 S | 2/1991 | Wenger et al. | |
| 5,032,919 A | 7/1991 | Randmae | |
| 5,295,490 A * | 3/1994 | Dodakian | A61B 5/1135 |
| | | | 600/534 |
| D345,905 S | 4/1994 | Hallgren | |
| 5,446,548 A | 8/1995 | Gerig et al. | |
| 5,692,719 A | 12/1997 | Shepherd et al. | |
| 5,914,660 A * | 6/1999 | Mesibov | G08B 21/0446 |
| | | | 340/517 |
| 5,996,814 A | 12/1999 | Workman et al. | |
| D421,447 S | 3/2000 | Eason et al. | |
| 6,113,455 A | 9/2000 | Whelan et al. | |
| D450,339 S | 11/2001 | Eason et al. | |
| 6,991,384 B1 | 1/2006 | Davis | |
| 7,035,432 B2 | 4/2006 | Szuba | |
| D519,990 S | 5/2006 | Lazor | |
| 7,177,386 B2 * | 2/2007 | Mostafavi | A61B 5/1135 |
| | | | 378/4 |
| D540,564 S | 4/2007 | Tai et al. | |
| D552,659 S | 10/2007 | Stephens et al. | |
| D553,848 S | 10/2007 | Barker et al. | |
| 7,277,122 B2 | 10/2007 | Sakai | |
| D557,035 S | 12/2007 | Huang et al. | |
| D557,320 S | 12/2007 | Fisher et al. | |
| D559,090 S | 1/2008 | Nawrocki | |
| 7,318,051 B2 | 1/2008 | Weston et al. | |
| 7,397,380 B1 | 7/2008 | Smolsky | |
| D574,159 S | 8/2008 | Howard | |
| 7,470,167 B2 | 12/2008 | Clark | |
| D585,395 S | 1/2009 | Cho et al. | |
| 7,477,285 B1 | 1/2009 | Johnson | |
| 7,624,074 B2 | 11/2009 | Weston et al. | |
| D606,106 S | 12/2009 | Kim et al. | |
| D614,223 S | 4/2010 | Kim et al. | |
| 7,696,888 B2 | 4/2010 | Swan et al. | |
| 7,720,259 B2 * | 5/2010 | Gordon | G06T 7/251 |
| | | | 348/169 |
| 7,774,032 B2 | 8/2010 | Swan et al. | |
| D624,108 S | 9/2010 | Wang et al. | |
| D624,109 S | 9/2010 | Wang et al. | |
| D627,815 S | 11/2010 | Oba et al. | |
| 7,827,631 B2 | 11/2010 | Holman | |
| 7,905,667 B2 | 3/2011 | Barker | |
| D635,940 S | 4/2011 | Cho et al. | |
| D640,692 S | 6/2011 | Waisman-Diamond | |
| D644,450 S | 9/2011 | Walter et al. | |
| D645,466 S | 9/2011 | Woo et al. | |
| D647,866 S | 11/2011 | Chen et al. | |
| D649,945 S | 12/2011 | Kim et al. | |
| D657,977 S | 4/2012 | Belitz | |
| D659,690 S | 5/2012 | Huang et al. | |
| 8,218,871 B2 | 7/2012 | Angell et al. | |
| D676,005 S | 2/2013 | Wood et al. | |
| D685,355 S | 2/2013 | Holleman et al. | |
| 8,461,996 B2 | 6/2013 | Gallagher | |
| 8,471,899 B2 * | 6/2013 | Johnson | G06F 19/321 |
| | | | 348/77 |
| 8,484,774 B2 | 7/2013 | Cohen | |
| 8,539,620 B1 * | 9/2013 | Wynh | A41B 13/06 |
| | | | 5/413 R |
| D692,939 S | 11/2013 | Huang et al. | |
| 8,638,364 B2 | 1/2014 | Chen et al. | |
| 8,640,280 B2 | 2/2014 | Gutierrez | |
| 8,646,126 B2 | 2/2014 | Carta | |
| 8,663,126 B1 * | 3/2014 | Al Thalab | A61B 5/0823 |
| | | | 600/529 |
| 8,675,059 B2 | 3/2014 | Johnson et al. | |
| 8,676,603 B2 | 3/2014 | Johnson et al. | |
| 8,836,751 B2 | 9/2014 | Ballantyne et al. | |
| D719,153 S | 12/2014 | Lim et al. | |
| D720,384 S | 12/2014 | Holmen et al. | |
| 8,922,653 B1 * | 12/2014 | Reeve | H04N 7/181 |
| | | | 348/143 |
| D722,637 S | 2/2015 | Baty et al. | |
| 8,953,674 B2 | 2/2015 | Henson | |
| D724,462 S | 3/2015 | Bould et al. | |
| D727,388 S | 4/2015 | Huang et al. | |
| D733,780 S | 7/2015 | Chen et al. | |
| 9,075,290 B1 | 7/2015 | Thieman | |
| D741,932 S | 10/2015 | Huang et al. | |
| D742,770 S | 11/2015 | Windstrup et al. | |
| 9,191,629 B2 | 11/2015 | Lee | |
| D746,350 S | 12/2015 | Li et al. | |
| 9,215,428 B2 | 12/2015 | Babineau et al. | |
| D746,709 S | 1/2016 | Heath et al. | |
| 9,268,465 B1 | 2/2016 | Yari | |
| D750,992 S | 3/2016 | Perez et al. | |
| D754,234 S | 4/2016 | Lee et al. | |
| D755,876 S | 5/2016 | Moss et al. | |
| 9,330,343 B2 | 5/2016 | Nakano | |
| D759,012 S | 6/2016 | Golden et al. | |
| D759,621 S | 6/2016 | Maxwell et al. | |
| D765,756 S | 9/2016 | Liu et al. | |
| 9,445,008 B2 * | 9/2016 | Yamazaki | H04N 5/2351 |
| D768,015 S | 10/2016 | Yang et al. | |
| D771,175 S | 11/2016 | Choi et al. | |
| D773,948 S | 12/2016 | Schneid et al. | |
| 9,530,080 B2 | 12/2016 | Glazer | |
| D778,192 S | 2/2017 | Bolger et al. | |
| D788,207 S | 5/2017 | Glazer et al. | |
| D793,996 S | 8/2017 | Katz et al. | |
| 9,721,180 B2 | 8/2017 | Prasad et al. | |
| D798,365 S | 9/2017 | Glazer et al. | |
| D798,366 S | 9/2017 | Glazer et al. | |
| D803,289 S | 11/2017 | Glazer et al. | |

(56) References Cited

U.S. PATENT DOCUMENTS

| | | | |
|---|---|---|---|
| D821,479 S | 6/2018 | Cabral et al. | |
| D822,641 S | 7/2018 | Belitz | |
| D824,681 S | 8/2018 | Vaughn | |
| D837,222 S | 1/2019 | Janzen et al. | |
| 2002/0097155 A1* | 7/2002 | Cassel | G08B 21/0453 340/573.1 |
| 2003/0057749 A1 | 3/2003 | Buono | |
| 2003/0233806 A1 | 12/2003 | Kuebler et al. | |
| 2004/0005083 A1 | 1/2004 | Fujimura et al. | |
| 2004/0005088 A1* | 1/2004 | Jeung | A61N 5/1049 382/128 |
| 2004/0082874 A1* | 4/2004 | Aoki | A61B 5/4818 600/534 |
| 2005/0034485 A1* | 2/2005 | Klefstad-Sillonville | A61B 5/4818 66/171 |
| 2005/0065655 A1 | 3/2005 | Hong et al. | |
| 2005/0069207 A1 | 3/2005 | Zakrzewski et al. | |
| 2005/0119560 A1 | 6/2005 | Mostafavi | |
| 2005/0244094 A1* | 11/2005 | Allsop | A61B 5/1077 385/13 |
| 2005/0285941 A1 | 12/2005 | Haigh et al. | |
| 2006/0028656 A1* | 2/2006 | Venkatesh | G01J 3/10 356/620 |
| 2006/0109375 A1 | 5/2006 | Ho et al. | |
| 2006/0262966 A1* | 11/2006 | Eck | A61B 6/12 382/128 |
| 2007/0058039 A1 | 3/2007 | Clark | |
| 2007/0073122 A1* | 3/2007 | Hoarau | A61B 5/14552 600/323 |
| 2007/0076935 A1 | 4/2007 | Jeung et al. | |
| 2007/0133975 A1 | 6/2007 | Lin | |
| 2007/0156060 A1 | 7/2007 | Cervantes | |
| 2007/0177792 A1 | 8/2007 | Ma et al. | |
| 2007/0200930 A1 | 8/2007 | Gordon | |
| 2007/0285259 A1 | 12/2007 | Desrosiers et al. | |
| 2007/0285570 A1 | 12/2007 | Desrosiers et al. | |
| 2008/0011344 A1 | 1/2008 | Barker | |
| 2008/0016624 A1 | 1/2008 | Osborn | |
| 2008/0077020 A1* | 3/2008 | Young | A61B 5/725 600/484 |
| 2008/0106421 A1* | 5/2008 | Adams | A61B 5/0002 340/573.1 |
| 2008/0107305 A1 | 5/2008 | Vanderkooy et al. | |
| 2008/0146911 A1* | 6/2008 | Miyake | A61B 5/08 600/411 |
| 2008/0180537 A1 | 7/2008 | Weinberg et al. | |
| 2008/0309765 A1 | 12/2008 | Dayan et al. | |
| 2009/0066671 A1 | 3/2009 | Kweon et al. | |
| 2009/0091617 A1 | 4/2009 | Anderson | |
| 2009/0278934 A1 | 11/2009 | Ecker et al. | |
| 2010/0060448 A1 | 3/2010 | Larsen et al. | |
| 2010/0134609 A1 | 6/2010 | Johnson | |
| 2010/0182136 A1* | 7/2010 | Pryor | F24C 7/082 340/425.5 |
| 2010/0202659 A1 | 8/2010 | Hamalainen | |
| 2010/0241018 A1 | 9/2010 | Vogel | |
| 2011/0044533 A1 | 2/2011 | Cobb | |
| 2011/0118608 A1 | 5/2011 | Lindner et al. | |
| 2011/0129210 A1 | 6/2011 | McGucken | |
| 2011/0230115 A1 | 9/2011 | Wang et al. | |
| 2011/0261182 A1 | 10/2011 | Lee et al. | |
| 2011/0295583 A1 | 12/2011 | Hollack et al. | |
| 2011/0310247 A1 | 12/2011 | Rensin | |
| 2011/0313325 A1 | 12/2011 | Cuddihy | |
| 2012/0002045 A1 | 1/2012 | Tony et al. | |
| 2012/0062735 A1 | 3/2012 | Rivera | |
| 2012/0069193 A1* | 3/2012 | Ramegowda | H04N 17/002 348/164 |
| 2012/0075464 A1 | 3/2012 | Derenne et al. | |
| 2013/0072823 A1 | 3/2013 | Kahn et al. | |
| 2013/0123639 A1* | 5/2013 | Ando | A61B 5/0059 600/473 |
| 2013/0144178 A1 | 6/2013 | Halperin et al. | |
| 2013/0169735 A1 | 7/2013 | Barker | |
| 2013/0182107 A1 | 7/2013 | Anderson | |
| 2013/0241730 A1 | 9/2013 | Saitwal et al. | |
| 2013/0250063 A1 | 9/2013 | Lee et al. | |
| 2013/0296716 A1* | 11/2013 | Kurzenberger | G06K 7/10366 600/479 |
| 2013/0342691 A1* | 12/2013 | Lewis | H04N 5/23209 348/143 |
| 2013/0342693 A1 | 12/2013 | Lee | |
| 2014/0046231 A1* | 2/2014 | Barlow | A61B 5/024 601/100 |
| 2014/0070957 A1* | 3/2014 | Longinotti-Buitoni | G06F 3/011 340/870.01 |
| 2014/0072206 A1 | 3/2014 | Eaton | |
| 2014/0092247 A1 | 4/2014 | Clark et al. | |
| 2014/0121540 A1 | 5/2014 | Raskin | |
| 2014/0140592 A1 | 5/2014 | Lasenby et al. | |
| 2014/0142435 A1* | 5/2014 | Bernal | A61B 5/091 600/476 |
| 2014/0160349 A1 | 6/2014 | Huang et al. | |
| 2014/0168397 A1 | 6/2014 | Greco et al. | |
| 2014/0204207 A1 | 7/2014 | Clark et al. | |
| 2014/0247334 A1 | 9/2014 | Johnson et al. | |
| 2014/0253709 A1 | 9/2014 | Bresch et al. | |
| 2014/0267625 A1 | 9/2014 | Clark et al. | |
| 2014/0270494 A1 | 9/2014 | Sawhney et al. | |
| 2014/0288968 A1 | 9/2014 | Johnson | |
| 2014/0334058 A1 | 11/2014 | Galvan et al. | |
| 2014/0336479 A1* | 11/2014 | Ando | A61B 5/14551 600/310 |
| 2015/0045608 A1* | 2/2015 | Karp | A61M 21/02 600/28 |
| 2015/0094606 A1* | 4/2015 | Mestha | A61B 5/4818 600/534 |
| 2015/0105608 A1* | 4/2015 | Lipoma | A61B 5/1115 600/27 |
| 2015/0105670 A1 | 4/2015 | Bresch et al. | |
| 2015/0109441 A1 | 4/2015 | Fujioka | |
| 2015/0141762 A1* | 5/2015 | Heinrich | A61B 5/4806 600/301 |
| 2015/0288877 A1* | 10/2015 | Glazer | G06K 9/00335 348/77 |
| 2015/0302717 A1 | 10/2015 | Denittis et al. | |
| 2016/0015278 A1* | 1/2016 | Campo | G06T 7/0016 348/143 |
| 2016/0074764 A1 | 3/2016 | Chen | |
| 2016/0183695 A1 | 6/2016 | Veron | |
| 2016/0328993 A1* | 11/2016 | Brogioli | A61B 5/0816 |
| 2016/0345832 A1 | 12/2016 | Pavagada Nagaraja et al. | |
| 2017/0095170 A1 | 4/2017 | Verkurijsse et al. | |
| 2017/0319114 A1* | 11/2017 | Kaestle | A61B 5/0077 |
| 2019/0098260 A1* | 3/2019 | Glazer | A61B 5/4815 |
| 2019/0205655 A1* | 7/2019 | Matsuoka | G06K 9/00228 |

FOREIGN PATENT DOCUMENTS

| | | |
|---|---|---|
| WO | 1999049656 A1 | 9/1999 |
| WO | 2013016603 A1 | 1/2013 |
| WO | 2013170032 A2 | 11/2013 |
| WO | 2014012070 A1 | 1/2014 |
| WO | 2015091582 A1 | 6/2015 |
| WO | 2017196695 A2 | 11/2017 |

OTHER PUBLICATIONS

Derpanis., "Overview of the RANSAC Algorithm", New York University, Version 1.2, 2 pages, May 13, 2010.

Felzenszwalb et al., "Object Detection with Discriminatively Trained Part Based Models", IEEE Transactions on Pattern Analysis and Machine Intelligence, vol. 32, Issue 9, pp. 1627-1645, Sep. 2009.

Glazer et al., "One-Class Background Model", ACCV 2012: Computer Vision—ACCV Workshops, pp. 301-307, 2012.

Weinland., "A Survey of Vision-Based Methods for Action Representation, Segmentation and Recognition", Institut National De Recherche En Informatique Et En Automatique, Research Report RR-7212, 54 pages, Feb. 2010.

(56) References Cited

OTHER PUBLICATIONS

Poppe., "Vision-based human motion analysis: An overview", Computer Vision and Image understanding 108, pp. 4-18, 2007.
Moeslund et al., "A Survey of Computer Vision-Based Human Motion Capture", Computer Vision and Image Understanding 81, pp. 231-268, 2001.
Kientz, et al., "KidCam: Toward an Effective Technology for the Capture of Children's Moments of Interest", Proceedings of 7th International Conference on Pervasive Computing, pp. 115-132, Nara, Japan, May 11-14, 2009.
U.S. Appl. No. 29/608,324 office action dated Sep. 20, 2018.
Viola et al., "Rapid Object Detection Using a Boosted Cascade of Simple Features", Proceedings of IEEE Computer Society Conference on Computer Vision and Pattern Recognition, vol. 1, pp. 511-218, Feb. 2001.
Lam et al., "Mobile Video Stream Monitoring System", Proceedings of the 11th ACM International Conference on Multimedia, 2 pages, Nov. 2-8, 2003.
Raskar, et al., "Prakash: Lighting Aware Motion Capture using Photosensing Markers and Multiplexed Illuminators", ACM Transactions on Graphics, vol. 26, No. 3, Article 36, 12 pages, Jul. 2007.
Alcantarilla et al., "KAZE Features", Proceedings of European Conference on Computer Vision, pp. 214-227, vol. 7577, Florence, Italy, Oct. 7-13, 2012.
Alcantarilla et al., "Fast Explicit Diffusion for Accelerated Features in Nonlinear Scale Spaces", 24th British Machine Vision Conference (BMVC), Bristol, UK, 11 pages, Sep. 9-13, 2013.
NANIT—Camera/Floorstand assembly, 6 pages, Retrieved on Aug. 13, 2018 (published date unknown) https://support.nanit.com/hc/en-us/articles/235605608-Camera-Floor-stand-assembly.
International Application # PCT/US2018/62166 search report dated Feb. 19, 2019.
NANIT, "NANIT Smart Baby Monitor and Wall Mount", pp. 1-10, Dec. 9, 2017.
U.S. Appl. No. 29/612,968 office action dated Feb. 5, 2019.
NANIT Camera and floor stand, 1 page, Retrieved on Mar. 29, 2017 (published date unknown) https://store.nanit.com/.
Cowboystudio Photography Photo Studio Flash Mount Three Umbrellas Kit With Light Stand (online), http://www.sears.com/cowboystudio-photography-photo-studio-flash-mount-three/p-SPM8700940502?plpSellerId=AmiVentures Inc&prdNo-2&blockNo=2&blockType=G2#>, 3 pages, Retrieved on Feb. 24, 2017 (published date unknown).
Nest Cam Indoor security camera, 1 page, Retrieved on Mar. 1, 2017 (published date unknown) https://www.amazon.com/Nest-Indoor-security-camera-Amazon/dp/B00WBJGUA2?psc=1>.
Flir FX Portable Interchangeable Wi-Fi Camera, 2 pages, Mar. 6, 2014 http://geeknewscentral.com/2014/03/06/flir-fx-portable-interchangeable-wi-fi-camera/>.
NANIT Multi-Stand, 4 pages, Dec. 5, 2016 https://www.amazon.com/Nanit-N102-Multi-Stand-White/dp/B01MDKHTL7.
NANIT, "How do I reset my Nanit camera?", 2 pages, Dec. 9, 2016 https://support.nanit.com/hc/en-us/articles/235804047-How-do-I-reset-my-Nanit-camera.
Glazer et al., U.S. Appl. No. 29/612,968, filed Aug. 6, 2017.
Glazer et al., U.S. Appl. No. 16/091,989, filed Oct. 7, 2018.
European Application # 17796611.6 search report dated Jan. 15, 2020.
European Application # 17796611.6 search report dated Nov. 7, 2019.
U.S. Appl. No. 16/091,989 office action dated Nov. 29, 2019.
CN Application # 2017800264834 office action dated Jan. 3, 2020.

\* cited by examiner

RESPIRATION MONITOR

CROSS-REFERENCE TO RELATED APPLICATION

This application claims the benefit of U.S. Provisional Patent Application 62/589,587, filed Nov. 22, 2017, which is incorporated herein by reference.

FIELD OF THE INVENTION

The present invention relates generally to sleep monitoring, and particularly to apparatus, systems and methods for video-based monitoring of a sleeping infant.

BACKGROUND

Video-based sleep monitors for infants are known in the art. For example, U.S. Pat. No. 8,922,653 describes a crib mobile and surveillance system which communicates video data captured by a camera within a mobile member housing, and sounds received by a microphone disposed in a base, to a handheld monitor. The video data are displayed and broadcast in real time on a monitor screen on the handheld monitor to remotely monitor a child lain in a crib having the present device.

U.S. Pat. No. 9,530,080, whose disclosure is incorporated herein by reference, describes systems and methods for monitoring babies with cameras using a centralized computation and storage center that allows using visual output signals for computer vision and machine learning analysis and high-level reasoning of baby movements. The system comprises a camera located at a predefined working point above a baby's crib, and one or more communication networks between components of the system including a web-based network for in-depth computer vision and machine learning analysis of the visual output signals by an analysis server.

PCT International Publication WO 2017/196695, whose disclosure is incorporated herein by reference, describes a video monitoring system, which includes a camera head, including an infrared illumination source and an image sensor. A mount is configured to hold the camera head in a fixed location and orientation above a crib, so that the image sensor captures images of the crib and an intervention region adjacent to the crib from a fixed perspective.

As another example, U.S. Patent Application Publication 2013/0342693 describes a video-enabled baby monitoring system including a transmitter with a camera feature, which captures motion and includes microprocessors that generate a series of video signal codes, which are transmitted at specific radio frequencies to a dedicated receiver unit. The transmitter unit also includes an infrared light source and a sound capture source, wherein the sound capture source generates sound signal codes. Another unit provides for enhanced, convenient data transfer from the transmitter unit and may be selected from a number of adaptor docking stations; or a smart phone platform; or a docking cradle with Wi-Fi capability.

Systems for monitoring the breathing of a sleeping person are also known in the art. For example, U.S. Patent Application Publication 2004/0005083 describes a method and system for monitoring breathing movement of an infant and for detecting and predictably estimating regular cycles of breathing movements. Another disclosed aspect of the invention is directed to detect and report irregularity of breathing activity of an infant, such as cessation and non-periodicity, which suggests a likelihood of SIDS.

U.S. Patent Application Publication 2015/0105670 relates measurement of vital signs such as a respiratory rate or a heart rate. In particular, a system for determining a vital sign of a subject comprises an imaging unit for obtaining video data of the subject, a marker directly or indirectly attached to a body of the subject, wherein the marker comprises a graphical pattern, an image processing unit for detecting said marker in said video data, and an analysis unit adapted to extract a vital sign parameter related to the vital sign of the subject from said video data and to determine the vital sign from said vital sign parameter.

U.S. Patent Application Publication 2016/0345832 describes a system and method for monitoring biological status through contactless sensing that includes a sensing device with at least one video imaging device; a sensor data processing unit, wherein the sensor processing unit when in a respiratory sensing mode is configured to extract a set of primary components of motion from image data from the video imaging device; a biological signal processor that when in a respiratory sensing mode is configured to identify at least one dominant component of motion and generate a respiratory signal; and a monitor system.

SUMMARY

Embodiments of the present invention that are described hereinbelow provide systems and methods for monitoring respiration of a sleeping infant or other human subject.

There is therefore provided, in accordance with an embodiment of the invention, a system for respiration monitoring, including a garment, which is configured to be fitted snugly around a body of a human subject, and which includes, on at least a portion of the garment that fits around a thorax of the subject, a pattern of light and dark pigments having a high contrast at a near infrared wavelength. A camera head is configured to be mounted in proximity to a bed in which the subject is to be placed, and includes an image sensor and an infrared illumination source, which is configured to illuminate the bed with radiation at the near infrared wavelength, and is configured to transmit a video stream of images of the subject in the bed captured by the image sensor to a processor, which analyzes movement of the pattern in the images in order to detect a respiratory motion of the thorax.

In some embodiments, the human subject is an infant, the bed is a crib, and the garment includes a swaddling cloth. In one embodiment, the swaddling cloth is configured as a sack, having a size and shape suitable for containing the body of the infant. Alternatively, the swaddling cloth is configured as a band, having a size and shape suitable to surround the thorax of the infant.

In a disclosed embodiment, the pattern extends around both a front and a back of the thorax when the garment is fitted around the body of the subject.

In some embodiments, the pattern includes an arrangement of light or dark geometrical shapes, which repeat across at least the portion of the garment, and the processor is configured to identify and track the geometrical shapes in the images in order to analyze the movement. In a disclosed embodiment, the shapes have respective corners, and the processor is configured to identify and track the corners in the images in order to analyze the movement.

Additionally or alternatively, the processor is configured to calibrate a scale of the images responsively to a distance between the repeating shapes. In one embodiment, the processor is configured to apply the scale in measuring the respiratory motion. Additionally or alternatively, the processor is configured to apply the scale in measuring one or more dimensions of the subject.

In a disclosed embodiment, the processor is configured to identify, responsively to the movement of the pattern, a deviation of at least one of an amplitude and a rate of the respiratory motion from a predefined normal range, and to issue an alert in response to the deviation.

There is also provided, in accordance with an embodiment of the invention, a method for respiration monitoring, which includes providing a garment, which is configured to be fitted snugly around a body of a human subject, and which includes, on at least a portion of the garment that fits around a thorax of the subject, a pattern of light and dark pigments having a high contrast at a near infrared wavelength. A bed in which the subject is placed is illuminated with radiation at the near infrared wavelength. A video stream of images of the subject in the bed is captured while illuminating the bed at the near infrared wavelength. Movement of the pattern in the images is analyzed in order to detect a respiratory motion of the thorax.

The present invention will be more fully understood from the following detailed description of the embodiments thereof, taken together with the drawings in which:

DETAILED DESCRIPTION OF EMBODIMENTS

Overview

Concern over proper respiration leads many parents of young infants to monitor their child's nighttime breathing. A wide range of product offerings exist for this purpose, but they tend to be uncomfortable, unreliable, or both.

Embodiments of the present invention that are described herein offer a new solution to the problem of infant respiration monitoring, using a novel garment, which facilitates both reliable detection of respiratory motion and infant comfort, while fitting snugly around the infant's body. ("Snug" in this context means that the garment fits tightly enough so that the cloth will expand and contract as the infant's thorax expands and contracts in respiration, without being so tight as to constrict respiratory motion.)

Substantially any suitable type of garment can be used for the present purposes. By way of example, the embodiments described below refer specifically to a swaddling cloth, such as a swaddling sack, having a size and shape suitable for containing the entire body of the infant, or a swaddling band, which fits around the thorax. The use of a swaddling cloth is advantageous in promoting both sound sleep and reliable monitoring. The principles of the present invention, however, are by no means limited to this type of garment, and may alternatively be applied in monitoring the respiration of other subjects, including older children, as well as adults.

Regardless of the specific configuration, the garment comprises a pattern of light and dark pigments on at least a portion of the garment that fits around the thorax of the subject. The light and dark pigments are chosen so that the pattern has a high contrast at a near infrared (NIR) wavelength, meaning specifically a wavelength between 800 nm and 1500 nm. This wavelength range is useful due to the availability of intense, inexpensive solid-state light sources, such as light-emitting diodes (LEDs), and the sensitivity of common image sensors in this range, while being invisible to human eyes. The terms "light" and "dark" in relation to the pigments mean, in the context of the present description and in the claims, that the "light" pigment reflects at least 50% of the incident radiation at a chosen illumination wavelength in the NIR, while the "dark" pigment reflects less than 20% of the incident light at this wavelength. The term "high contrast" in this context means that when the pattern is illuminated uniformly at the chosen wavelength, the intensity of reflected light received by the image sensor from the light pigment is at least twice that received from the dark pigment.

In the disclosed embodiments, a camera head is mounted in proximity to a bed in which the subject is to be placed. The camera comprises an image sensor and an infrared illumination source, which illuminates the crib at a chosen wavelength in the NIR. The image sensor captures images of the subject in the bed (for example, of an infant in a crib, as shown in the figures that are described below). The camera head transmits a video stream of these images to a processor, which analyzes movement of the pattern in the images in order to detect the respiratory motion of the thorax. When the processor detects a deviation of the amplitude and/or rate of the respiratory motion from a predefined normal range, it issues an alert and thus enables a caregiver to intervene immediately. The garment can be designed so that the pattern extends around both the front and the back of the thorax; the respiratory motion can thus monitored reliably regardless of whether the subject is lying on his or her front, back or side. Alternatively, the pattern may appear only the front of the thorax.

In some embodiments, the pattern comprises an arrangement of light or dark geometrical shapes, which repeat periodically across at least the portion of the garment that extends across the thorax. This sort of pattern facilitates fast and accurate processing of the images by the processor. For example, the processor can identify corners of the geometrical shapes and track these corners in the images in order to analyze the movement of the pattern.

When the actual, physical sizes of the shapes on the swaddling cloth are known, the processor can calibrate the scale of the images based on the distance (in pixels) between the repeating shapes in the images, and can then apply this scale in measuring the respiratory motion and/or measuring one or more dimensions of the subject. These latter measurements include, but are not limited to, the distance an infant being monitored traveled in a crib, the distance crawled, the magnitude of head movements, the magnitude of limb movements, the magnitude of twitches, head circumference, head shape, head volume, height, body volume, weight and BMI estimations, limb length, distance between the eyes, forehead height, general facial dimensions, shoulder width, hip width, hip angles, foot angles, torso length. The calibrated scale can also be used to improve object detection algorithms by normalizing the image size to minimize the size tolerance of detection of objects such as the crib, the infant, and its head.

Although the figures and the embodiments described below refer to certain specific swaddling cloth designs, with a certain pattern shown by way of example, other sorts of garments and other patterns that can be used for the present purposes will be apparent to those skilled in the art after reading the present description. All such alternative embodiments are considered to be within the scope of the present invention.

System Description

Figure 1:
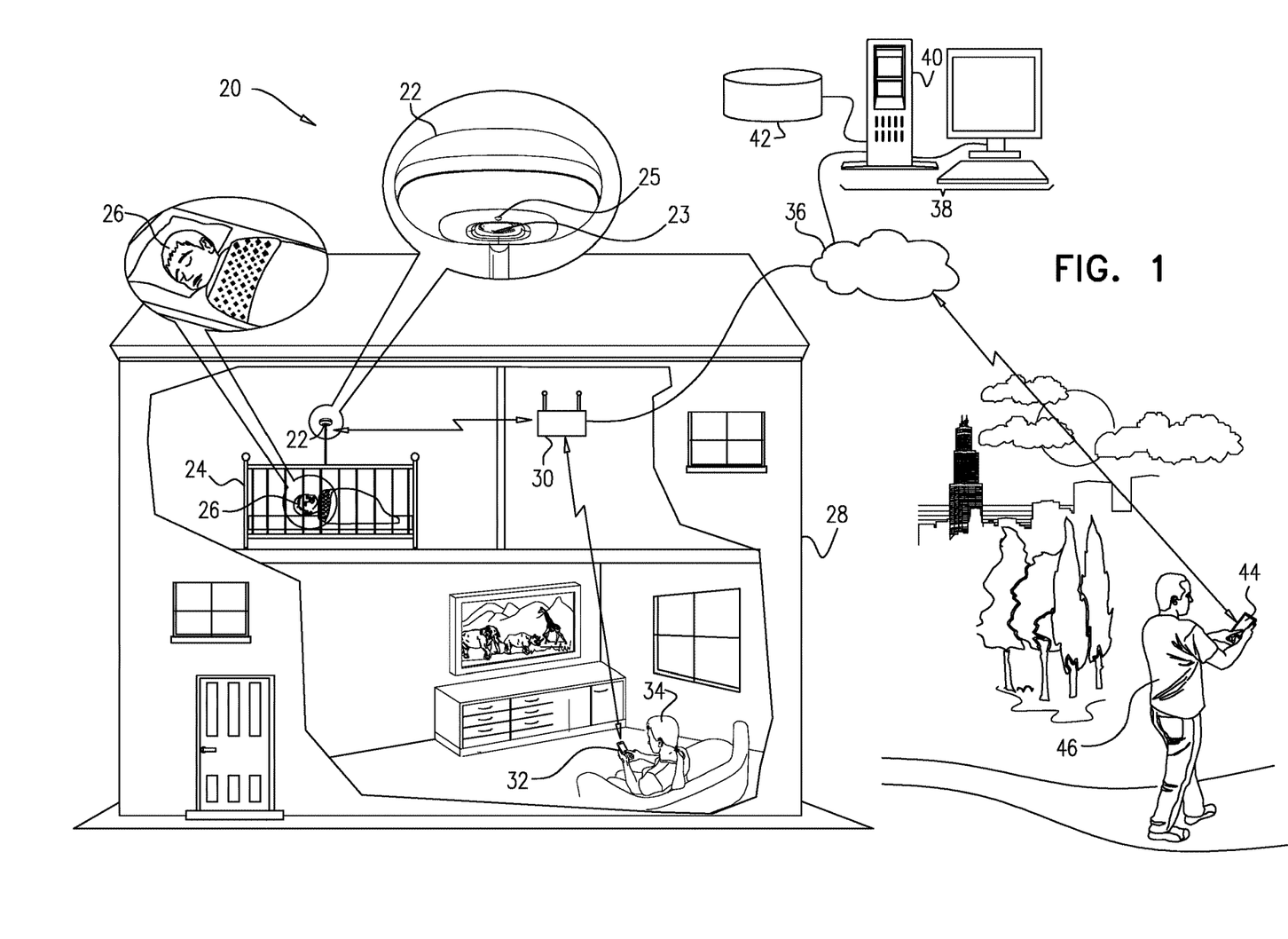
FIG. 1 is a block diagram that schematically illustrates a system for infant sleep monitoring, in accordance with an embodiment of the invention.

FIG. 1 is a block diagram that schematically illustrates a system 20 for infant sleep monitoring, in accordance with an embodiment of the invention. System 20 comprises a monitoring camera head 22, which is mounted in a fixed location and orientation above a crib 24, in which an infant 26 is sleeping in a residence 28. Alternatively, camera head 22 may be mounted in another suitable location in proximity to the crib, mounted on a wall or tabletop, for example.

For purposes of image capture, an infrared (IR) light-emitting diode (LED) 25 on the lower side of camera head 22 illuminates the sleeping infant 26. A diffuser can be used to spread the infrared light uniformly across the crib. Camera head 22 also comprises an infrared-sensitive image sensor 23, which may conveniently have a standard 4:3 aspect ratio to fit the size of a standard crib 24. The resolution and sensitivity of image sensor 23 can be optimized for night conditions, and specifically for the wavelength range of LED 25. Further details of camera head 22, including its internal components and modes of operation, are described in the above-mentioned PCT International Publication WO 2017/196695 (particularly in FIGS. 4A/B and 5 and the corresponding description in the specification on pages 8-9). This PCT publication also describes different ways of mounting the camera head above or alongside the crib.

Camera head 22 transmits digitized streaming video, and possibly other signals, as well, over a local network to a router 30, typically via a wireless local area network (LAN) link, such as a Wi-Fi connection, or a wired link, such as an Ethernet connection. Camera head 22 transmits the digitized video data in packets that are addressed so that router 30 forwards the video packets both to a local client device 32 on the local network and via a public network 36, such as the Internet, to a remote server 38. Client device 32 typically comprises a smart phone, tablet or personal computer, which enables a caregiver 34 in another room of residence 28 to monitor infant 26, even when there is no Internet connection available. Server 38 makes video images and other data available to authorized remote client devices 44, thus enabling a caregiver 46 to monitor infant 26 at any location where there is access to public network 36. The Wi-Fi or other local network connection provides reliable video streaming from camera head 22 to client device 32 with high bandwidth and low latency, even if the external Internet connection is not working. As long as the Internet is connected, however, the video stream is also transmitted to server 38 for purposes of analysis and retransmission.

Server 38 typically comprises a general-purpose computer, comprising a processor 40 and a memory 42, which receives, stores and analyzes images from camera head 22 in residence 28 and similarly from other cameras in other residences (not shown). In the present embodiment, processor 40 analyzes the images in order to detect and measure respiratory motion of the thorax of infant 26, and to provides caregivers 34 and 46 with reports and (when required) alerts regarding the infant's breathing patterns. Processor 40 typically performs these functions under the control of software, which may be downloaded to server 38 in electronic form, over a network, for example, as well as stored on tangible, non-transitory computer-readable media, such as magnetic, optical or electronic memory media. Alternatively or additionally, some or all of these processing and monitoring functions may be performed locally, for example by a microprocessor in camera head 22 and/or by suitable application software running on processors in client devices 32 and/or 44.

Figure 2:
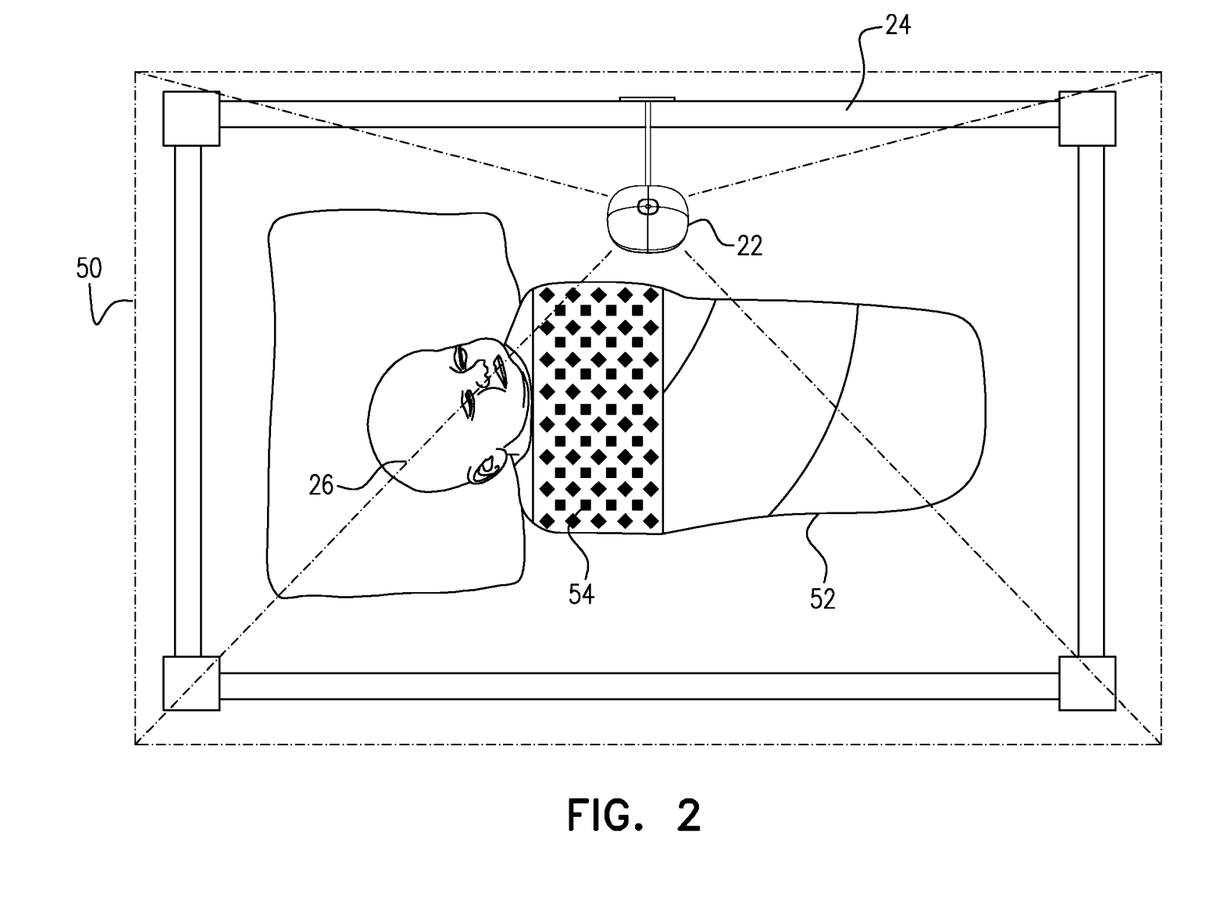
FIG. 2 is a schematic top view of a sleep monitoring device mounted over an infant's crib, in accordance with an embodiment of the invention.

FIG. 2 is a schematic top view showing details of the deployment and use of monitoring camera head 22 over crib 24, in accordance with an embodiment of the invention. Infant 26 in crib 24 is wrapped in a swaddling sack 52, with a periodic pattern printed on a portion 54 of the swaddling sack that fits around the infant's thorax. In this embodiment, monitoring camera head 22 stands against a wall over crib 24. Camera head 22 is held, for example, at the end of an arm at the upper end of a tripod mount behind crib 24, at the midpoint of the long side of the crib. Camera head 22 in this embodiment is positioned and adjusted so that the camera head has a field of view 50 from a fixed perspective that encompasses at least the area of crib 24. This perspective provides server 38 with image information that can be analyzed conveniently and reliably to detect respiratory motion of infant 26. Alternatively, the camera head may be mounted in any other suitable location in proximity to crib 24 that gives a view of the infant that is suitable for monitoring movement of the pattern on the swaddling cloth or other garment.

Figure 3A:
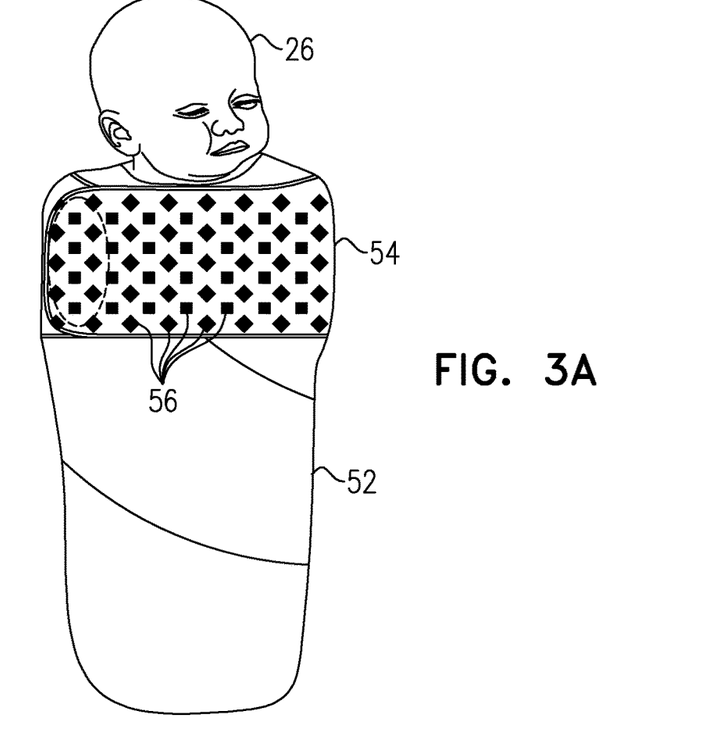
FIGS. 3A and 3B are schematic front and back views, respectively, of a swaddling sack used in monitoring respiration of an infant, in accordance with an embodiment of the invention.
Figure 3B:
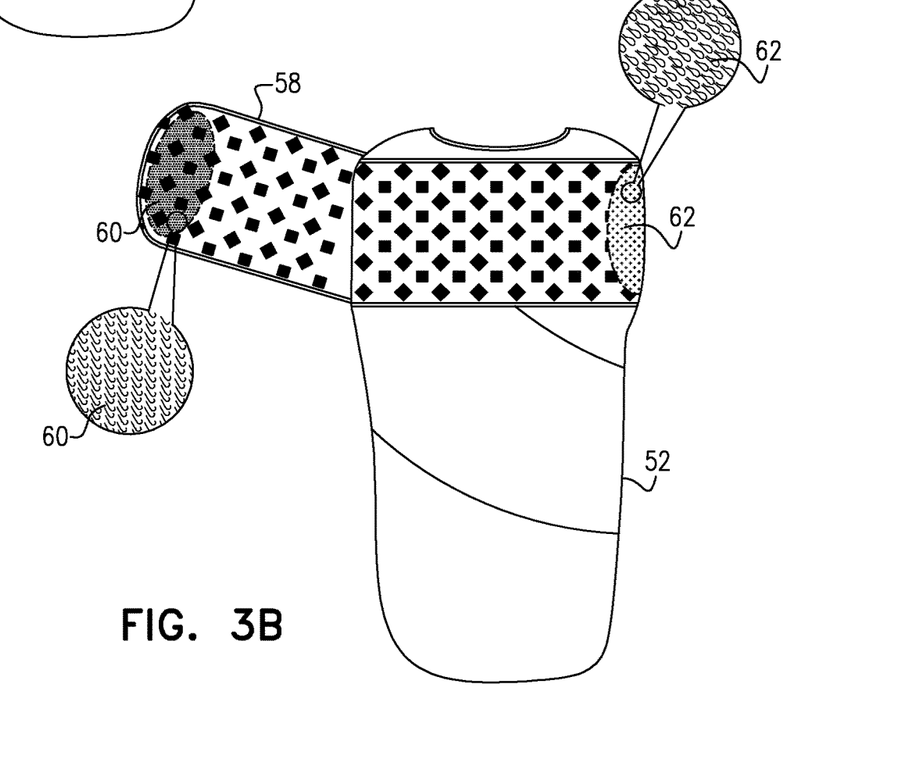

FIGS. 3A and 3B are schematic front and back views, respectively, of swaddling sack 52, which is used in monitoring the respiration of infant 26, in accordance with an embodiment of the invention. Before putting infant 26 into crib 24, the caregiver inserts the infant into swaddling sack 52, and then fastens a band 58 snugly around the infant's thorax. Hook and loop patches 60 and 62 (such as Velcro® patches) may be used for this purposes, or any other suitable type of fastener that is known in the art.

Portion 54 of swaddling sack 52 comprises a periodic pattern of light and dark pigments, extending around both the front and back of sack 52, with a high contrast at the near infrared wavelength of LED 25. In this example, the pattern comprises two types of dark geometrical shapes 56, but alternatively other patterns may be used, with one or more different shapes, in either dark or light pigment. The sharp corners of the shapes in this example facilitate detection and tracking of the shapes by an image processor for the purpose of detecting respiratory motion. The dimensions of shapes 56 are typically between 5 and 50 mm, and camera head is designed so that each shape will have an extent between 3 and 30 pixels in the images captured by image sensor 23, although larger or smaller shapes and magnifications may alternatively be used.

Figure 4A:
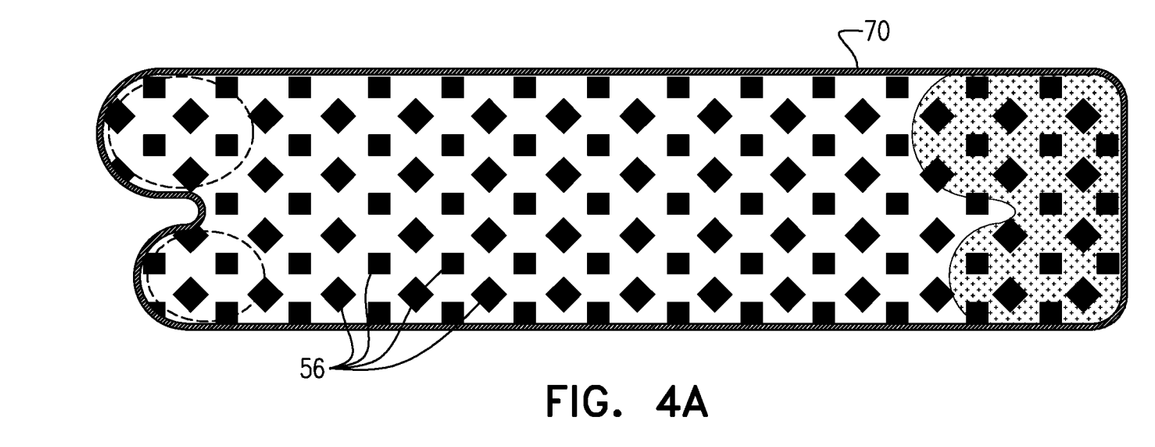
FIGS. 4A and 4B are schematic outer and inner views, respectively of a swaddling band used in monitoring respiration of an infant, in accordance with another embodiment of the invention.
Figure 4B:
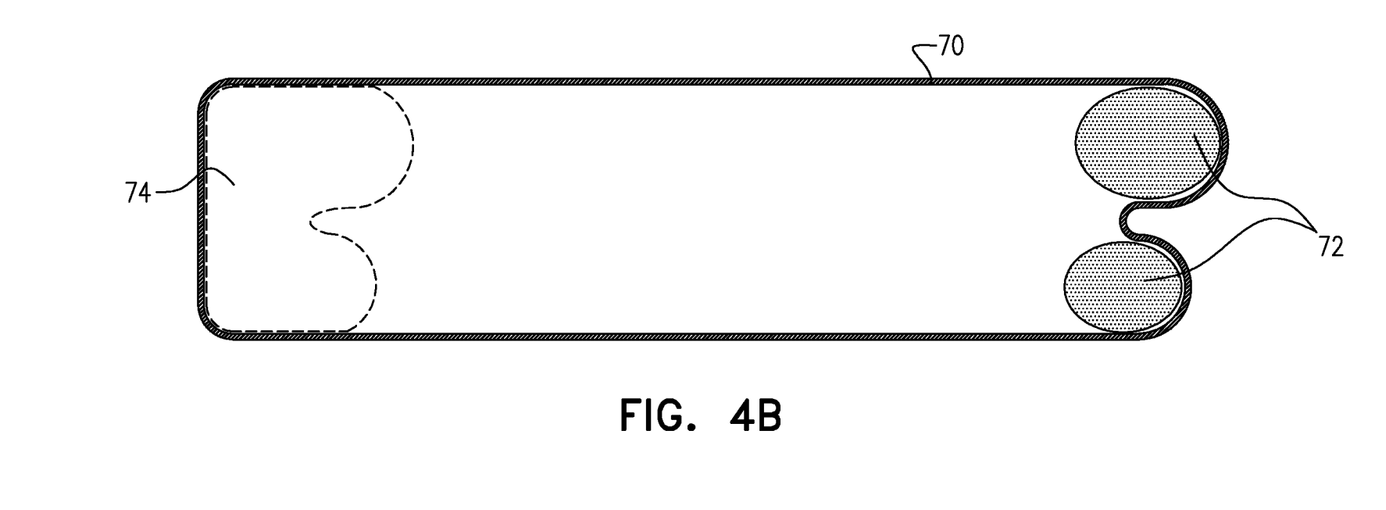

FIGS. 4A and 4B are schematic outer and inner views, respectively, of a swaddling band 70 used in monitoring respiration of an infant, in accordance with another embodiment of the invention. The size and shape of band 70 are suitable to surround the thorax of an infant, with the band fastened snugly around the thorax by hook and loop patches 72 and 74. Band 70 leaves the infant free to move his or her arms and legs, in contrast to sack 52. The pattern of shapes 56 on band 70 is similar to that on sack 52, as described above.

Monitoring of Respiratory Motion

Figure 5:
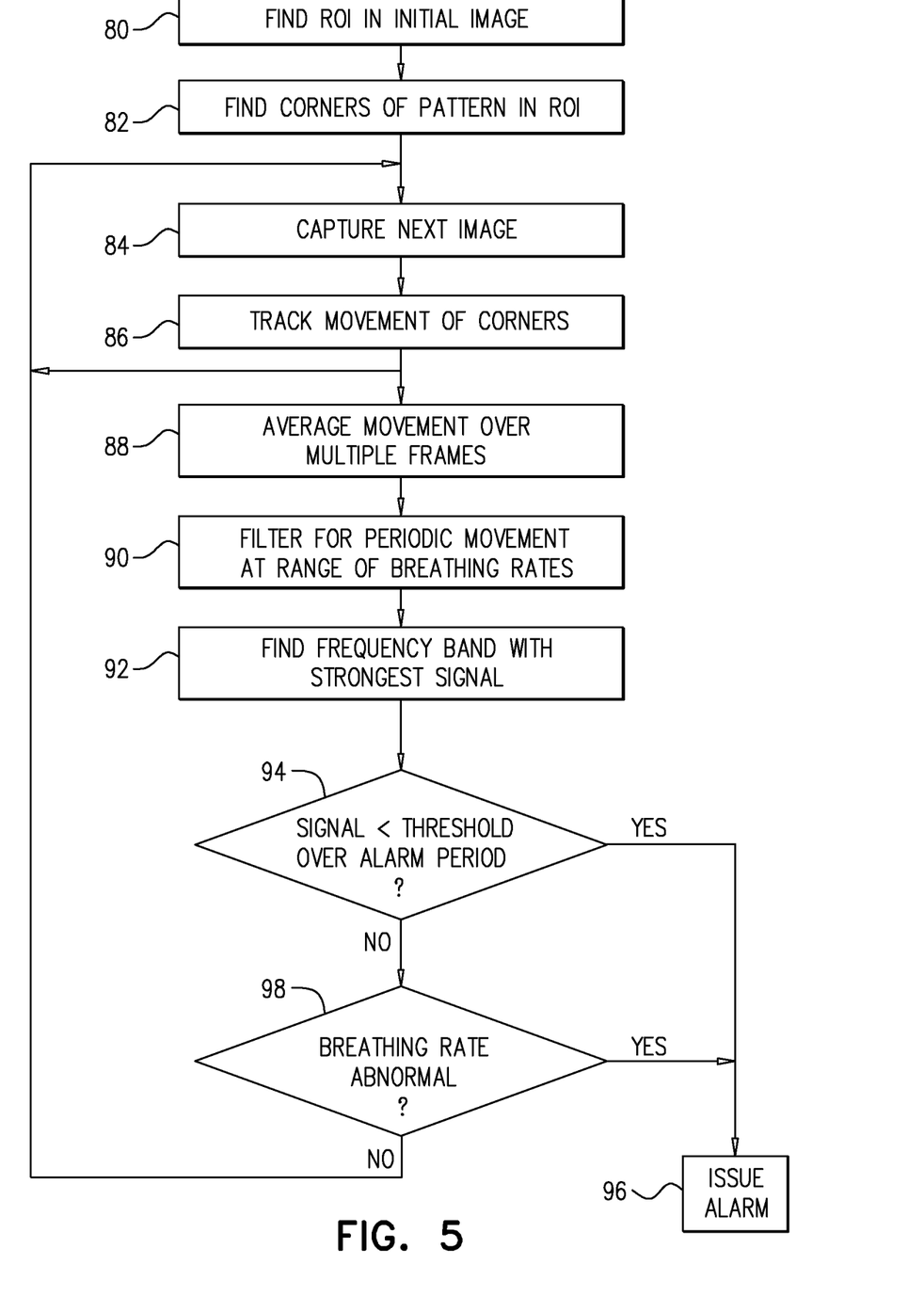
FIG. 5 is a flow chart that schematically illustrates a method for respiration monitoring, in accordance with an embodiment of the invention.

FIG. 5 is a flow chart that schematically illustrates a method for respiration monitoring, in accordance with an embodiment of the invention. This method is described hereinbelow, for the sake of concreteness and clarity, with reference to the elements of system 20 and swaddling sack 52, as shown and described above. Alternatively, the method may be applied, mutatis mutandis, in other system configurations and/or using other sorts of swaddling cloth, as noted earlier. Specifically although certain image processing functions and communication functions are described below as being carried out by server 38, at least some of these functions may be carried out by other means, such as client devices 32 and 44 and/or a processor (not shown) that is embedded in camera head 22.

Processor 40 initiates the method of FIG. 5 upon receiving a video stream from camera head 22 and a signal (for example from the camera head or from client device 32) indicating that monitoring is to begin. Processor 40 finds a region of interest (ROI) that contains a part of the pattern on swaddling sack 52 in an initial image frame, at an ROI identification step 80. The ROI may be identified automatically by analyzing the image to locate the pattern on swaddling sack 52 (or swaddling band 70, for example). Processor 40 may access features of the pattern or patterns that are used on various types of swaddling cloth, such as the sizes and forms of shapes 56, in memory 42, in order to identify the ROI more easily. Alternatively or additionally, the caregiver may indicate the location of the ROI to the processor, for example by pointing to the ROI in an image from camera head 22 that is displayed on client device 32.

In some embodiments, processor 40 finds the locations of the corners of shapes 56 in the ROI on swaddling sack 52, at a corner finding step 82. ("Corners" are not necessarily right angles, and can be formed that the meeting point of edges at different angles, for example angles ranging between 60° and 120°.) Corners can be found by filtering the part of the image that is contained in the ROI with filters that are matched to the geometrical features of the pattern, for example. Once the corners are found, processor 40 can calibrate the scale of the images by comparing the distance between the repeating shapes in the images to the known distance between the geometrical features on the swaddling sack.

Once the ROI and pattern features have been identified in the initial image, processor 40 receives and processes succeeding images in the video stream, at an image input step 84. In each image, the processor tracks the movement of each of the corners in the ROI that was identified previously. This step may use techniques such as feature mapping or the Kanade-Lucas-Tomasi (KLT) feature tracking algorithm in order to measure motion from frame to frame with sub-pixel accuracy. If the ROI is lost in a given image or sequence of images, for example due to large movements of infant 26, processor 40 may search over an entire image in order to recover the location of the ROI and may then return to step 80.

Alternatively or additionally, processor 40 may apply other sorts of image processing algorithms in identifying and tracking movement of the pattern, not necessarily depending on corners. For example, template shift registration can be used to track shapes having no clear corners (such as circles). As another example, normal flow algorithms can be used in tracking object edges.

Since respiratory movement from one frame to the next is very small, processor 40 averages the motion of each corner (or other feature) over multiple successive frames and/or multiple feature locations, at a movement averaging step 88. When infant 26 is breathing, the infant's thorax expands and contracts periodically, so that all of the corners within a given ROI on swaddling sack 52 will move in the same direction from frame to frame, with a temporal variation that is approximately sinusoidal. The average movement will therefore be substantial. (The ROI is chosen at step 80 to be large enough to contain multiple shapes 56, but small enough so that all the shapes in the ROI move in the same direction during respiration.) On the other hand, when infant 26 is not breathing, the directions of movement of the different corners will be random and will thus cancel out upon averaging. Processor 40 may also identify large movements that are not periodic as corresponding to the infant moving in his or her sleep or being awake.

Processor 40 analyzes the averaged movement signal over time in order to detect periodic motion that is characteristic of respiration, at a movement analysis step 90. For this purpose, processor 40 may filter the averaged signal using a set of bandpass filters with frequency bands distributed through the range of normal respiration frequencies. For example, processor 40 may apply a set of six bandpass filters that together span the normal breathing range, which is about 20-60 breaths/minute for infants under one year old. Any suitable type of bandpass filter with sufficiently sharp edges may be used for this purpose, for instance a fifth-order Butterworth filter, as is known in the art. Alternatively, larger or smaller numbers of filters, of this or other types, may be used, depending upon the available computing power and the level of precision that is required to avoid false alarms.

After filtering the signal at step 90, processor 40 chooses the frequency band with the highest amplitude, at a band selection step 92. Processor 40 compares this amplitude to a preset threshold, at a motion checking step 94. If the amplitude is below threshold, and remains below threshold for longer than a preset time limit, processor 40 issues an alert, at an alarm step 96. Infants may normally stop breathing for short periods, typically up to 20 sec, and then resume breathing normally. The time limit at step 94 may thus be set, for example, to 20 sec. If processor 40 does not detect respiratory motion of sufficient amplitude over a period longer than this limit, it may send a notification to client device 32 at step 96, for instance, or take more drastic action, such as triggering a visible and/or audible alarm in residence 28. For example, processor 40 may activate a visible light and/or audio speaker in camera head 22.

When processor 40 detects respiratory motion of sufficient amplitude at step 94, it also checks the infant's respiratory frequency, at a rate checking step 98. If the highest motion amplitude was found to be in the highest or lowest frequency band of the filters applied at step 92, for example, the processor may conclude that the breathing rate is abnormally high or low. In this case, too, processor 40 will issue an alert at step 96. Otherwise, the processor concludes that the infant's breathing is normal and continues to capture and analyze further images as described above. Optionally, processor 40 may continually issue updates to client devices 32 and 44, even when infant 26 is breathing normally, to indicate the breathing status and respiratory rate of the infant.

As noted earlier, although the embodiments described above relate specifically to infant respiration monitoring, using a patterned swaddling cloth, the principles of the present invention may similarly be applied using other sorts of garments with suitable pattern, not only for infants but also for older subjects. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A system for respiration monitoring, comprising:
    a band, having a size and shape suitable to surround and be fastened snugly around a thorax of an infant, and which comprises a pattern of light and dark pigments having a high contrast at a near infrared wavelength and extending around a front, a back and sides of the thorax, while leaving the infant free to move his or her arms and legs; and
    a camera head, which is configured to be mounted in proximity to a bed in which the infant is to be placed, and which comprises an image sensor and an infrared illumination source, which is configured to illuminate the bed with radiation at the near infrared wavelength, and which is configured to transmit a video stream of images of the infant in the bed captured by the image sensor to a processor, which analyzes movement of the pattern in the images in order to detect a respiratory motion of the thorax regardless of whether the infant is lying on his or her front, back or side.

2. The system according to claim 1, wherein the pattern comprises an arrangement of light or dark geometrical shapes, which repeat across at least the portion of the garment, and wherein the processor is configured to identify and track the geometrical shapes in the images in order to analyze the movement.

3. The system according to claim 2, wherein the shapes have respective corners, and wherein the processor is configured to identify and track the corners in the images in order to analyze the movement.

4. The system accordingly to claim 2, wherein the processor is configured to calibrate a scale of the images responsively to a distance between the repeating shapes.

5. The system according to claim 4, wherein the processor is configured to apply the scale in measuring the respiratory motion.

6. The system according to claim 4, wherein the processor is configured to apply the scale in measuring one or more dimensions of the infant.

7. The system according to claim 1, wherein the processor is configured to identify, responsively to the movement of the pattern, a deviation of at least one of an amplitude and a rate of the respiratory motion from a predefined normal range, and to issue an alert in response to the deviation.

8. A method for respiration monitoring, comprising:
    providing a band, having a size and shape suitable to surround and be fastened snugly around a thorax of an infant, and which comprises a pattern of light and dark pigments having a high contrast at a near infrared wavelength and extending around a front, a back and sides of the thorax, while leaving the infant free to move his or her arms and legs; and
    illuminating a bed in which the infant is placed with radiation at the near infrared wavelength;
    capturing a video stream of images of the infant in the bed while illuminating the bed at the near infrared wavelength; and
    analyzing movement of the pattern in the images in order to detect a respiratory motion of the thorax regardless of whether the infant is lying on his or her front, back or side.

9. The method according to claim 8, wherein the pattern comprises an arrangement of light or dark geometrical shapes, which repeat across at least the portion of the swaddling garment, and wherein analyzing the movement comprises identifying and tracking the geometrical shapes in the images.

10. The method according to claim 9, wherein the shapes have respective corners, and wherein identifying and tracking the geometrical shapes comprises identifying and tracking the corners in the images.

11. The method accordingly to claim 9, wherein identifying and tracking the geometrical shapes comprises calibrating a scale of the images responsively to a distance between the repeating shapes.

12. The method according to claim 11, wherein analyzing the movement comprises applying the scale in measuring the respiratory motion.

13. The method according to claim 11, and comprising applying the scale in measuring one or more dimensions of the infant.

14. The method according to claim 8, wherein analyzing the movement comprises identifying, responsively to the movement of the pattern, a deviation of at least one of an amplitude and a rate of the respiratory motion from a predefined normal range, and issuing an alert in response to the deviation.

15. The method according to claim 11, and comprising analyzing the movement so as to measure a distance traveled by the infant in the bed.

16. The system according to claim 1, wherein the pattern is printed over an entire area of the band.

17. The system according to claim 1, wherein the band comprises hook and loop patches, which fasten the band snugly around the thorax of the infant.

* * * * *